United States Patent [19]

Tsai

[11] 4,336,290

[45] Jun. 22, 1982

[54] PALLADIUM ALLOYS FOR FUSION TO PORCELAIN

[75] Inventor: Min H. Tsai, Van Nuys, Calif.

[73] Assignee: Unitek Corporation, Monrovia, Calif.

[21] Appl. No.: 254,005

[22] Filed: Apr. 13, 1981

[51] Int. Cl.$^3$ ............................ A61K 6/04; C22C 5/04
[52] U.S. Cl. ...................................... 428/76; 433/207; 428/450; 420/463
[58] Field of Search ............. 75/172 R; 433/200, 207; 428/76, 450

[56] References Cited

U.S. PATENT DOCUMENTS 4,261,744  4/1981  Boyajian ........................... 75/172 R
4,319,877  3/1982  Boyajian ............................ 433/207

Primary Examiner—L. Dewayne Rutledge
Assistant Examiner—Alan E. Schiavelli
Attorney, Agent, or Firm—Richard H. Brink

[57] ABSTRACT

A semi-precious alloy for use in a dental restoration which does not discolor porcelain and remains ductile after firing of a porcelain jacket thereon. The alloy is 80–90% palladium, 5–15% indium, 1–5% gallium, 0.1–0.5% aluminum, 0.1–0.5% silicon, and 0.01–1.0% of at least one element from ruthenium and osmium.

11 Claims, No Drawings

PALLADIUM ALLOYS FOR FUSION TO PORCELAIN

FIELD OF THE INVENTION

This invention relates to a semi-precious alloy for use in dental restoration.

BACKGROUND OF THE INVENTION

Noble metal alloys adapted for ceramic bonding (the application of a porcelain jacket or covering) are well known in dentistry and are used in the manufacturing of crowns, bridges, and other prosthetic appliances. These so called noble "ceramic alloys" typically consist of 80-90% gold, 5-15% platinum and 1-10% palladium. The newer alloys consist of 51.5% gold, 8.5% indium, 1.5% gallium, and 38.5% palladium. Alloys of this type and application of such alloys in dentistry are discussed in detail in U.S. Pat. No. 3,413,723, Wagner and Pralow and in U.S. Pat. No. 4,123,262, Cascone. For brevity, the disclosures of these patents are incorporated herein by reference.

Due to the increase in price of gold and platinum, lower cost palladium alloys were developed. U.S. Pat. No. 3,929,474, discloses a palladium-silver system. U.S. Pat. No. 3,819,366, discloses a palladium-indium-silver or palladium-indium-silver-gold system. Palladium alloys contain silver which causes discoloration in porcelain as described by R. V. Williams, Jr., et al in Dental Porcelain: The State of the Art 1977, Henry N. Yamada, editor, 1977, University of Southern California School of Dentistry, Los Angeles, CA, pages 71-77. U.S. Pat No. 3,928,913 discloses a palladium-cobalt alloy for ceramic bonding. It is difficult to match the shades of the porcelain due to the formation of blue oxide during the firing process.

Coloration of porcelain may be limited by baking one layer of gold powder onto the understructure of the alloy prior to the application of dental porcelain. However, this technique increases cost (gold powder and labor), and causes uncertainty of porcelain/metal bond strength. The introduction of certain elements described in U.S. Pat. No. 4,194,907, overcomes the discoloration problem with respect to certain alloys. Another way to avoid this problem is the elimination of the use of silver or cobalt as described by Prosen in U.S. Pat. No. 4,046,561, U.S. Pat. No. 4,124,382, and U.S. Pat. No. 4,179,288. Prosen continuously works to improve the ductility of the alloy which is an important characteristic of dental alloys especially when margins of the crown needed to be burnished.

The object of this invention is to develop a palladium alloy which forms a light shade of oxide during the firing of porcelain. The oxide does not discolor the porcelain. Another object of this invention is to develop a palladium alloy which remains ductile even after the firing processes of porcelain.

SUMMARY OF THE INVENTION

This invention relates to a semi-precious castable alloy suitable for fusing with dental porcelain. The alloy does not discolor porcelain and remains ductile after fusing with porcelain. This alloy is also substantially lower in cost than precious metal alloys.

According to this invention, the palladium alloy consists of 80-90% palladium, 5-15% indium, 1-5% gallium, 0.1-0.5% aluminum, 0.1-0.5% silicon, and 0.01-1.0% of ruthenium, osmium or a mixture thereof.

In method terms, the invention contemplates the technique of making a dental restoration by firing a porcelain jacket over a cast body of an alloy having the aforesaid composition.

Accordingly, this invention has provided an improved semi-precious castable alloy which overcomes the problems presented with prior alloys.

DESCRIPTION OF THE PREFERRED EMBODIMENT

The semi-precious dental alloy of this invention has the following elemental components and acceptable ranges thereof (percentages are by weight):

| ELEMENT | ACCEPTABLE RANGES (%) |
| --- | --- |
| Palladium | 80-90 |
| Indium | 5-15 |
| Gallium | 1-5 |
| Aluminum | 0.1-0.5 |
| Silicon | 0.1-0.5 |
| Ruthenium, Osmium or a mixture thereof | 0.01-1.0 |

The preferred composition of this invention is 84.8% palladium, 11.2% indium, 3.5% gallium, 0.15% aluminum, 0.20% silicon, 0.07% ruthenium, and 0.08% osmium.

The relatively high palladium content provides satisfactory corrosion resistance when the alloy is exposed to mouth fluids. Indium and gallium are used to lower the melting temperature of palladium and also to increase the fluidity of the molten metal for casting. Silicon is used to lighten up the dark bluish grey color of the oxide of the palladium-indium-gallium alloy which is formed during the baking process of porcelain. Silicon content is preferably limited to less than 0.5%. If the silicon content is over 0.5% the melting temperature of the alloy will be too low for the porcelain to be baked onto the alloy without causing distortion in the understructure around 950° C. Aluminum is used to stabilize the light grey oxide formed during the firing process of the alloy. Without the aluminum in the alloy, light grey oxide is easy to peel off. Use of aluminum preferably does not exceed 0.5% because the hardness of the alloy will be too high. Osmium and ruthenium are used to avoid hot tear in the castings.

The components are alloyed by induction melting in an argon atmosphere. The molten alloy is then poured into water to form shot for remelting. Conventional techniques are used to make a finished dental restoration with the alloy. An investment mold is prepared by using the conventional lost-wax or burn-out plastic methods. The alloy is then melted and poured in the mold which is mounted in a centrifugal casting machine. After cooling, the mold is broken away and the casting cleaned, polished, and finished in preparation for application of dental porcelains by the usual firing techniques.

The alloy has been tested and proved satisfactory when bonded thermally to dental porcelain available from Vita Zahnfabrik under the trademark VMK-68. Other compatible porcelain materials are available from Dentsply International, Inc. (under the trademark "Biobond") and from the Ceramco Division of Johnson & Johnson.

Discoloration of the dental porcelain is observed by fusing one of the light shade porcelains, shade $A_1$, for example, onto the understructure of the alloy. Ductility of the alloy is tested by bending a 1.0 mm diameter wire cast from the alloy, after the wire has gone through all the porcelain firing cycles. The alloy lacks ductility if the 1.0 mm diameter wire is fractured during bending.

The following examples are intended to illustrate the invention claimed herein without unduly restricting it. A number of different alloys were tested in arriving at the preferred formulation and acceptable component ranges. Typical examples of these alloys are set forth below (the components being designated in percentage by weight):

| ELEMENT | EXAMPLE I | EXAMPLE II | EXAMPLE III | EXAMPLE IV |
| --- | --- | --- | --- | --- |
| Palladium | 84.8 | 80.0 | 85.0 | 87.0 |
| Indium | 11.2 | 14.5 | 10.8 | 8.7 |
| Gallium | 3.5 | 5.0 | 3.3 | 3.8 |
| Aluminum | 0.15 | 0.18 | 0.25 | 0.15 |
| Silicon | 0.20 | 0.20 | 0.25 | 0.20 |
| Ruthenium | 0.07 | 0.06 | 0.2 | 0.07 |
| Osmium | 0.08 | 0.06 | 0.2 | 0.08 |

The alloy of Example I did not discolor the porcelain. The alloy is very compatible with porcelain. The cast wire was bent to more than 135° without fracturing the cast wire. This indicates the alloy of Example I is ductile. The alloy of Example II did not discolor the porcelain. This alloy caused a checkline (small crack) in the porcelain under normal porcelain firing cycles. The checkline in the porcelain was healed (sealed) when the ceramometal structure was re-heated to 940° C. for six minutes and then cooled slowly to room temperature. This indicates the compositions of alloy II are at the lower end of the range to achieve good ceramic-metal compatibility. This alloy is also ductile. The alloy of Example III is ductile. This alloy has good ceramic-metal compatibility and does not cause any discoloration in the porcelain. However, this alloy is harder than alloy of Example I and II. This alloy may be used for long span bridges for which a harder alloy is needed. The alloy of Example IV is ductile. This alloy is compatible with porcelain and does not discolor the porcelain.

Strength, elongation and modulus of elasticity are tested by using an Instrom tensile instrument. Vickers hardness is obtained by testing specimens of the alloy with a microhardness tester with diamond indenter. All these tests are fimilar to those skilled in the art. The Shell and Nielson technique (Shell, J. S. and Nielson, J. P., Journal of Dental Research 41, 1962 pp. 1424–1437) is used to determine bond strength of porcelain to metal.

Typical properties of the alloy of this invention are as follows:

| MECHANICAL PROPERTIES: (Baked Condition) | |
| --- | --- |
| Ultimate Tensile Strength: | 98,000 psi |
| Yield Strength (0.2% Offset): | 51,000 psi |
| Elongation (1 inch gage): | 14% |
| Modulus of Elasticity: | $18.5 \times 10^6$ psi |
| Hardness: | 220 D.P.H. |
| Porcelain Bond Strength: | 14,500 psi |
| Density: | 10.4 gm/cc |

Thus, according to this invention, an improved semi-precious castable alloy has been provided for use in dental restoration which does not discolor porcelain and is also ductile.

While this invention has been described and exemplified in terms of its preferred embodiment, those skilled in the art will appreciate that modifications can be made without departing from the spirit and scope of this invention.

What is claimed is:

1. A semi-precious castable dental alloy suitable for bonding with dental porcelain comprising about 80–90% palladium, 5–15% indium, 1–5% gallium, 0.1–0.5% aluminum, 0.1–0.5% silicon and 0.01–1.0% of a member selected from the group consisting of ruthenium, osmium and mixtures thereof.

2. A semi-precious castable dental alloy suitable for bonding with dental porcelain consisting essentially of:
   palladium: 80–90 percent;
   indium: 5–15 percent;
   gallium: 1–5 percent;
   aluminum: 0.1–0.5 percent; silicon: 0.1–0.5 percent; and
   ruthenium, osmium or a mixture thereof: 0.01–1.0 percent.

3. The alloy defined in claim 2 formed as a cast body for intra-oral installation and further comprising a porcelain jacket fired on the body.

4. The alloy defined in claim 2 wherein the constituent elements consist essentially of:
   palladium: 84.8 percent;
   indium: 11.2 percent;
   gallium: 3.5 percent;
   aluminum: 0.15 percent;
   silicon: 0.20 percent;
   ruthenium: 0.07 percent; and
   osmium: 0.08 percent.

5. The alloy defined in claim 2 wherein the constituent elements consist essentially of:
   palladium: 80.0 percent;
   indium: 14.5 percent;
   gallium: 5.0 percent;
   aluminum: 0.18 percent;
   silicon: 0.20 percent;
   ruthenium: 0.06 percent; and
   osmium: 0.06 percent.

6. The alloy defined in claim 2 wherein the constituent elements consist essentially of:
   palladium: 85.0 percent;
   indium: 10.8 percent;
   gallium: 3.3 percent;
   aluminum: 0.25 percent;
   silicon: 0.25 percent;
   ruthenium: 0.2 percent; and
   osmium: 0.2 percent.

7. The alloy defined in claim 2 wherein the constituent elements consist essentially of:
   palladium: 87.0 percent;
   indium: 8.7 percent;
   gallium: 3.8 percent;
   aluminum: 0.15 percent;
   silicon: 0.20 percent;
   ruthenium: 0.07 percent; and
   osmium: 0.08 percent.

8. The alloy defined in claim 4 formed as a cast body for intra-oral installation, and further comprising a porcelain jacket fired on the body.

9. The alloy defined in claim 5 formed as a cast body for intra-oral installation, and further comprising a porcelain jacket fired on the body.

10. The alloy defined in claim 6 formed as a cast body for intra-oral installation, and further comprising a porcelain jacket fired on the body.

11. The alloy defined in claim 7 formed as a cast body for intra-oral installation, and further comprising a porcelain jacket fired on the body.

* * * * *